United States Patent [19]

Downey

[11] Patent Number: 4,642,106
[45] Date of Patent: Feb. 10, 1987

[54] IMPLEMENT FOR EVACUATING THE CONTENTS OF DRAINABLE OSTOMY POUCHES

[76] Inventor: William Downey, P.O. Box 135, Clinton, N.Y. 13323

[21] Appl. No.: 576,442

[22] Filed: Feb. 2, 1984

[51] Int. Cl.[4] ............................................. A61F 5/44
[52] U.S. Cl. .................................... 604/332; 604/333; 128/760
[58] Field of Search ................. 128/1, 57, 303 R, 325, 128/346; 604/332–345; 222/101–103; 128/760

[56] References Cited

U.S. PATENT DOCUMENTS

| | | | |
|---|---|---|---|
| 2,083,603 | 6/1937 | Harwick | 221/60 |
| 3,648,702 | 3/1972 | Bean | 128/321 |
| 3,687,131 | 8/1972 | Rayport et al. | 128/346 |
| 4,164,223 | 8/1979 | Munib | 128/346 |
| 4,287,890 | 9/1981 | Fogarty | 128/303 R |
| 4,320,787 | 3/1982 | McMorrow | 128/767 |
| 4,387,713 | 6/1983 | Calanni | 604/333 |

OTHER PUBLICATIONS

"The Surgical Armontarium; American V. Mueller Co., Chicago, Ill. 60648, 1980.

Primary Examiner—Stephen C. Pellegrino
Assistant Examiner—J. L. Kruter
Attorney, Agent, or Firm—Charles S. McGuire

[57] ABSTRACT

A manually manipulated implement and method of use thereof for facilitating the drainage of conventional ostomy pouches are disclosed. The implement includes a two-piece handle portion with an elongated engagement member extending from each, with hinge means connecting the handle pieces and engagement members of movement toward and away from one another between spaced and essentially contacting positions. When the pouch drain opening is positioned over a suitable receptacle, the pouch walls are placed between the elongated engagement members, which are then moved from the spaced position to engage the pouch walls firmly therebetween. The implement is then moved manually toward the drain opening, forcing the contents out of the pouch, into the receptacle. In the preferred embodiment the implement is of one-piece molded plastic construction and includes means for stabilizing the relative lateral position of the engagement members as the implement is moved along the pouch.

4 Claims, 3 Drawing Figures

IMPLEMENT FOR EVACUATING THE CONTENTS OF DRAINABLE OSTOMY POUCHES

BACKGROUND OF THE INVENTION

The present invention relates to novel implements for and methods of emptying the contents of a conventional ostomy pouch and, more specifically, to a simple, manually manipulated instrument and method of use thereof in facilitating evacuation of the contents of an ostomy pouch.

Surgical procedures providing substitute paths for evacuation of body wastes necessitated by removal or lack of function of basic elements of the gastrointestinal or urinary tracts have been successfully practised for many years. For example, the two principal types of surgeries involving the intestinal tract are colostomy and ileostomy. A number of variants of these procedures, as well as other types of ostomy surgery are commonly performed, over one million Americans being ostomates and over 100,000 more people in the United States undergoing ostomy surgery each year.

The bowel waste and other effluent diverted through the colon to the surface of the abdomen is discharged through a surgically-created exit or "stoma" into a flexible bag or pouch having an opening communicating therewith. The cost of the pouches, and frequency with which they must be emptied and/or replaced, often makes it economically unfeasible to discard the pouches with each replacement. Thus, drainable pouches are conventionally used to permit emptying the contents through an opening in one end, remote from the stoma-communicating opening, into a suitable receptacle, whereby the pouch remains attached to the stoma for continuous use through multiple emptying cycles.

The emptying of the pouch is performed manually, removing the clamp normally sealing the drainage opening and directing the effluent into a toilet or other receptacle. The pouch is usually squeezed manually and may be flushed with water to complete the emptying operation. The pouch, particularly the end having the drainage opening, is wiped with tissues and the clamp replaced. The procedure is almost always very messy and disagreeable.

It is the principal object of the present invention to provide an improved means and method of emptying ostomy pouches.

A further object is to provide a manually manipulated implement of simple, inexpensive design which greatly facilitates the task of emptying osotomy pouches.

Another object is to provide a method of emptying the contents of drainable ostomy pouches with the aid of a manually manipulated implement.

Other objects will in part be obvious and in part appear hereinafter.

SUMMARY OF THE INVENTION

In accordance with the foregoing objects, the invention contemplates an implement which, in the preferred embodiment, is formed as a single, unitary piece of molded plastic. The implement includes a handle portion having two pieces joined at one end by a hinge formed by a flexible, reduced-section portion of the plastic material.

Extending from each of the two handle pieces are elongated engagement members which are movable to a position engaging the pouch walls therebetween. The implement is then moved to force the effluent from the pouch through the drainage opening. Preferably, means are provided to restrain the position of the engagement members against movement in a direction transverse to the plane of the hinged member movement.

In an alternate embodiment, the engagement members are connected to the handle pieces for rotary movement. In this case, the engagement members are separate from the handle pieces and are attached thereto for rotary movement about their elongated axes.

DETAILED DESCRIPTION

Figure 1:
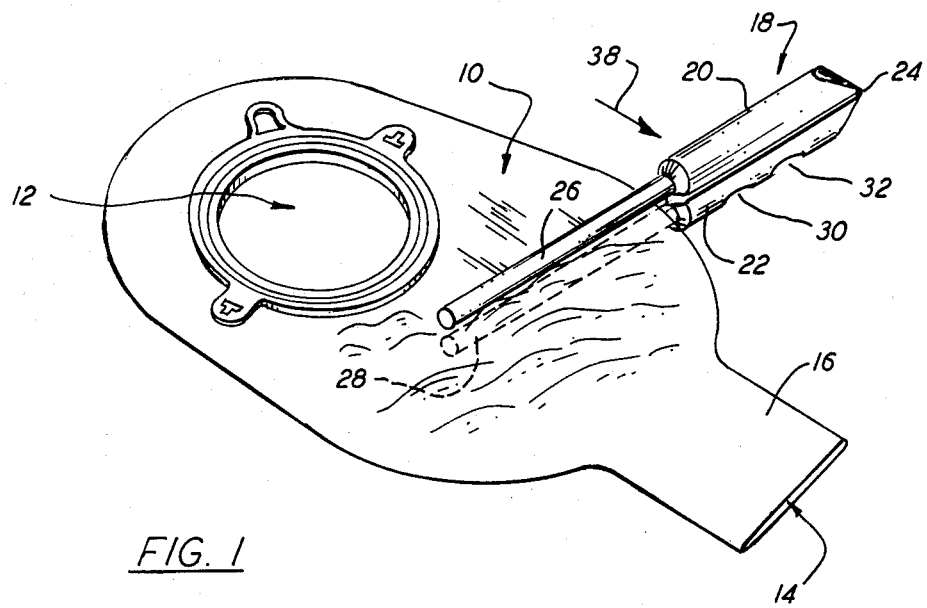
FIG. 1 is a perspective view of a typical ostomy pouch with an implement of the present invention engaged therewith for evacuation of the contents thereof.

Referring now to the drawings, in FIG. 1 is shown an ostomy pouch of conventional design, denoted generally by reference numeral 10, being of flexible material with upper and lower deformable walls, sealed together in the usual manner to form a hollow, impermeable structure. Pouch 10 includes a first opening 12 for sealing engagement with the stoma of an ostomy patient to receive the bowel waste or effluent passing from the body portion to which it is attached, in known manner. Second opening 14 is provided for drainage of the pouch contents after removal of a conventional clamp (not shown) which maintains the pouch in a sealed condition until the contents are to be emptied. Pouch 10, stoma-communicating opening 12 and drainage opening 14 are entirely conventional, the pouch being formed of a highly flexible, fluid impervous material such as a variety of plastics commonly used in such applications. Such pouches are also commonly provided with a neck 16 which is folded over and secured by the previously mentioned latch or clamp of conventional design.

When the pouch is to be emptied, the clamp is removed, neck 16 is unfolded to release opening 14, and the latter is directed over a toilet or other suitable receptacle, usually with opening 12 remaining in communication with the stoma. Evacuation of the pouch contents is then performed with the assistance of the manually manipulated implement of the present invention.

Figure 2:
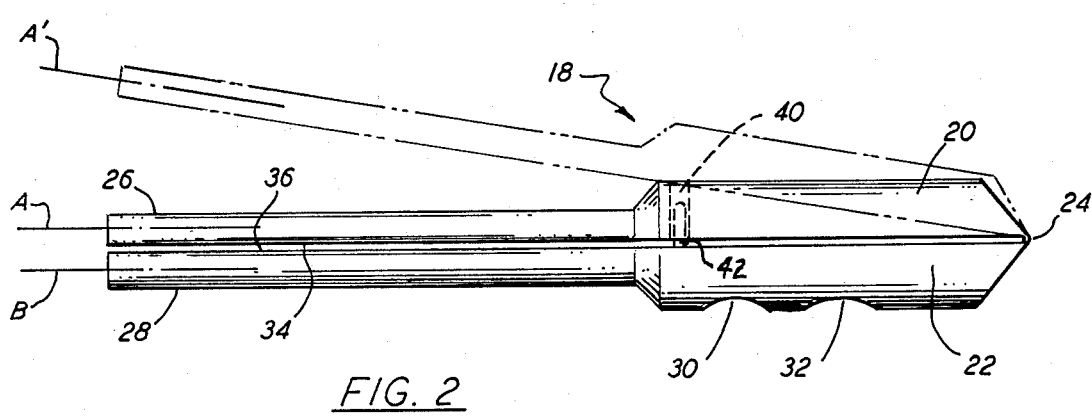
FIG. 2 is an elevational view of the preferred embodiment of the implement of the invention shown in two positions of movement.

As shown in FIGS. 1 and 2, implement 18 comprises a pair of handle pieces 20 and 22, joined by and movable about hinge members 24 of reduced section but preferably formed as part of the same, unitary, single piece of molded plastic as the rest of implement 18. Elongated engagement members 26 and 28 extend from handle pieces 20 and 22, respectively, being formed integrally therewith in the embodiment of FIGS. 1 and 2, along linear axes A and B which lie in a single plane and are perpendicular to the axis about which hinge 24 is movable.

The plastic material and condition in which it is molded preferably render implement 18 in a normal or unflexed position with engagement members 26 and 28 spaced apart from one another, as indicated by the dot-dash line position of handle piece 20 and engagement member 26 in FIG. 2. Grasping implement 18 in one hand with the thumb on handle portion 20 and two fingers on handle portion 22 (indented areas 30 and 32 being provided for such purpose) implement 18 is moved to a position wherein opposing surfaces 34 and 38 are in engagement with the walls of pouch 10, as shown in FIG. 1, axes A and B being substantially parallel.

With the walls of pouch 10 firmly grasped between surfaces 34 and 36 of engagement members 26 and 28 adjacent opening 12, implement 18 is moved in the direction of arrow 38 in FIG. 1. The engagement members slide over the surface of the pouch walls, forcing the contents out through opening 14. In the illustrated embodiment, the length of engagement members 26 and 28 is less than the width of pouch 10 but greater than one-half the width. Therefore, in order to complete the emptying of the pouch, the position of implement 18 is reversed and the engagement members are closed on the pouch from the opposite side and moved from a position adjacent opening 12 toward opening 14.

Engagement members 26 and 28 may be of circular cross section along their entire length, or of other shapes, e.g., with opposing surfaces 34 and 36 being flat. It is also preferred, since integrally formed hinge 24 may have some torsional flexibility, that the relative lateral positions of engagement members 26 and 28 be stabilized as the pouch is grasped therebetween and the implement moved toward the drain opening. Such stabilizing means are shown in FIG. 2, formed integrally with implement 18 and associated with the two handle pieces. Opening 40 is formed through handle piece 20 in alignment with protrusion 42 on handle piece 22. At least when implement 18 is moved to the position wherein engagement members 26 and 28 are engaging pouch 10, protrusion 42 is inserted in opening 40 with a close fit, restraining any relative lateral movement of handle pieces 20 and 22, and thereby of the engagement members during the emptying operation.

Figure 3:
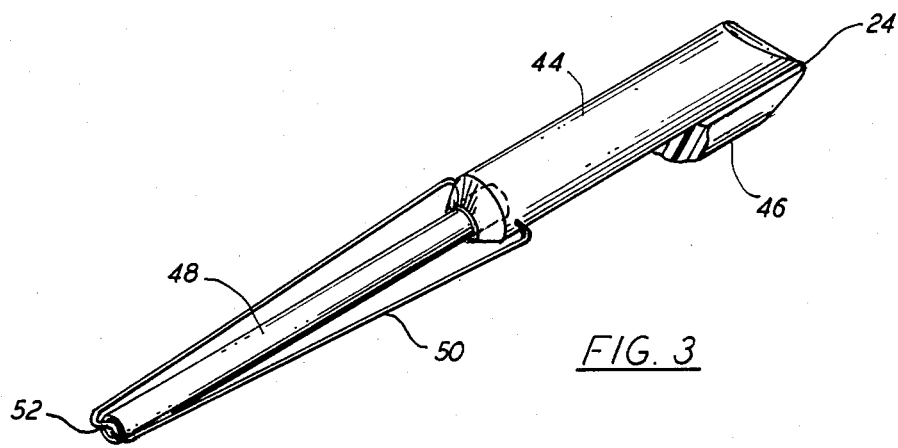
FIG. 3 is a fragmentary, perspective view of a portion of an alternate embodiment of the implement of the invention.

Turning now to FIG. 3, the pouch-cleaning implement is shown in a second embodiment wherein the engagement members are formed separately from the handle pieces and removably mounted thereon for rotation about their elongated axes. Handle pieces 44 and 46 are again joined at one end by integral hinge means 24, and are provided with an opening or socket at the other end. The engagement members, one of which is shown in FIG. 3 and denoted by reference numeral 48, are elongated and of circular cross section, fitting supply but rotatably within the handle piece sockets. Wire retainer 50 is connected by opposite end portions thereof to handle piece 44 for pivoting movement, and opposite end 52 is engaged in detent fashion with a depression in the outer end of engagement member 48. Handle portion 46 is provided with a socket and wire retainer (not shown) for securing the second engagement member thereto in the same way. In this embodiment, the engagement members roll, rather than slide, along the opposite walls of the pouch as the bag is emptied.

From the foregoing it may be seen that the objects and advantages of the invention are efficiently attained by a simple, inexpensive implement, preferably a one-piece plastic casting, and its manner of use, greatly reducing the disagreeable nature of the task of emptying the contents of ostomy pouches. The pouch may be emptied while remaining in the attached position, thus avoiding irritation of the skin surrounding the stoma which often results from frequent removal and replacement of the pouch.

What is claimed is:

1. A combination providing an ostomy pouch wearer with an improved emptying system, said combination comprising:
   (a) an essentially flat ostomy pouch having superposed, flexible walls of predetermined width and a drain opening at one end; and
   (b) a one-piece, molded plastic implement for manual manipulation in cooperative relationship with said pouch; said implement including:
      (i) a pair of manually engageable, elongated handle pieces extending along substantially linear axes;
      (ii) a pair of elongated engagement members respectively extending integrally from one end of said handle pieces along said linear axes; and
      (iii) integral hinge means connecting said handle pieces at the end of each opposite said one end to permit movement of said handle pieces, and thereby said engagement members, about a pivot axis substantially perpendicular to said linear axes, moving substantially in a single plane transverse to said pivot axis, between a first position, wherein said engagement members are spaced from one another to permit positioning thereof on opposite sides of said pouch walls, and a second position, wherein said engagement members are in closely spaced relation with portions of said pouch walls engaged therebetween, whereby said implement may be moved toward said drain opening with said engagement members in sliding contact with said pouch walls to force the contents of said pouch out through said drain opening.

2. The invention according to claim 1 wherein said engagement members have a length equal to one another and less than, but at least half, said predetermined width, whereby said implement may be manually manipulated to place said engagement members in contact with said pouch walls with said handle pieces on one side thereof and drawn toward said drain opening to empty at least a portion of the contents of said pouch, and the position of said implement reversed to contact said pouch walls with said handle portions on the other side thereof and drawn toward said drain opening to empty any remaining contents of said pouch.

3. The invention according to claim 1 and further including a protrusion on one and a mating opening in the other of said handle piece adjacent said one end of each, said protrusion and mating opening being so positioned on the respective handle pieces that said protrusion is positioned in said mating opening when said handle pieces are in said closed position, thereby restraining lateral movement of said handle pieces as said engagement members are drawn over said pouch walls.

4. The invention according to claim 1 wherein said engagement members are longer than said handle members.

* * * * *